US012667439B2

(12) United States Patent (10) Patent No.: US 12,667,439 B2

Poplaw (45) Date of Patent: Jun. 30, 2026

(54) COLORIZATION OF MEDICAL DEVICES IN ROBOTIC SURGERY USING AI AND MACHINE LEARNING

(71) Applicant: Clear Biopsy LLC, St. Joseph, MO (US)

(72) Inventor: Steven Poplaw, St. Joseph, MO (US)

(73) Assignee: Clear Biopsy LLC, St. Joseph, MO (US)

( * ) Notice: Subject to any disclaimer, the term of this patent is extended or adjusted under 35 U.S.C. 154(b) by 0 days.

(21) Appl. No.: 19/307,577

(22) Filed: Aug. 22, 2025

(65) Prior Publication Data

US 2026/0114943 A1 Apr. 30, 2026

Related U.S. Application Data

(60) Provisional application No. 63/711,850, filed on Oct. 25, 2024.

(51) Int. Cl.

| | |
|---|---|
| *A61B 34/30* | (2016.01) |
| *A61B 90/00* | (2016.01) |
| *G06T 7/00* | (2017.01) |
| *G06T 7/11* | (2017.01) |
| *G06T 7/50* | (2017.01) |
| *G06T 7/90* | (2017.01) |

(52) U.S. Cl.
CPC .............. *A61B 34/30* (2016.02); *A61B 90/37* (2016.02); *G06T 7/0008* (2013.01); *G06T 7/11* (2017.01); *G06T 7/50* (2017.01); *G06T 7/90*

(2017.01); *A61B 2034/301* (2016.02); *G06T 2207/10016* (2013.01); *G06T 2207/10136* (2013.01); *G06T 2207/20081* (2013.01)

(58) Field of Classification Search
USPC .......................................................... 345/589
See application file for complete search history.

(56) References Cited

U.S. PATENT DOCUMENTS

| | | | |
|---|---|---|---|
| 2014/0070111 A1* | 3/2014 | Rappaport ........... | G01N 33/227 |
| | | | 250/336.1 |
| 2020/0025696 A1* | 1/2020 | Potocek ................ | H01J 37/222 |
| 2020/0273581 A1* | 8/2020 | Wolf ...................... | G16H 40/63 |

(Continued)

*Primary Examiner* — James A Thompson
*Assistant Examiner* — Kim Thanh T Tran
(74) *Attorney, Agent, or Firm* — Bookoff McAndrews, PLLC

(57) ABSTRACT

A system for intraoperative medical instrument recognition may receive, from an imaging device positioned inside of a patient, a stream of intraoperative three-dimensional (3D) imaging data that includes anatomy of a patient and a medical instrument. The system may apply a material recognition algorithm to identify one or more objects formed of a predetermined material present in the intraoperative 3D imaging data. The system may apply a shape recognition algorithm to the one or more identified objects to identify the medical instrument. The system may generate a modified intraoperative imaging data stream in real-time with the receiving of the stream of intraoperative 3D imaging data. The modified intraoperative imaging data stream may include a visual characteristic, e.g., a colorization, applied to a region of the intraoperative 3D imaging data corresponding to the at least one identified medical instrument.

18 Claims, 6 Drawing Sheets
(2 of 6 Drawing Sheet(s) Filed in Color)

(56) References Cited

U.S. PATENT DOCUMENTS

2022/0160433 A1 * 5/2022 Rafii-Tari ........... A61B 17/3403
2023/0317252 A1 * 10/2023 Zhang ................... G06V 10/44
                                                                382/128

* cited by examiner

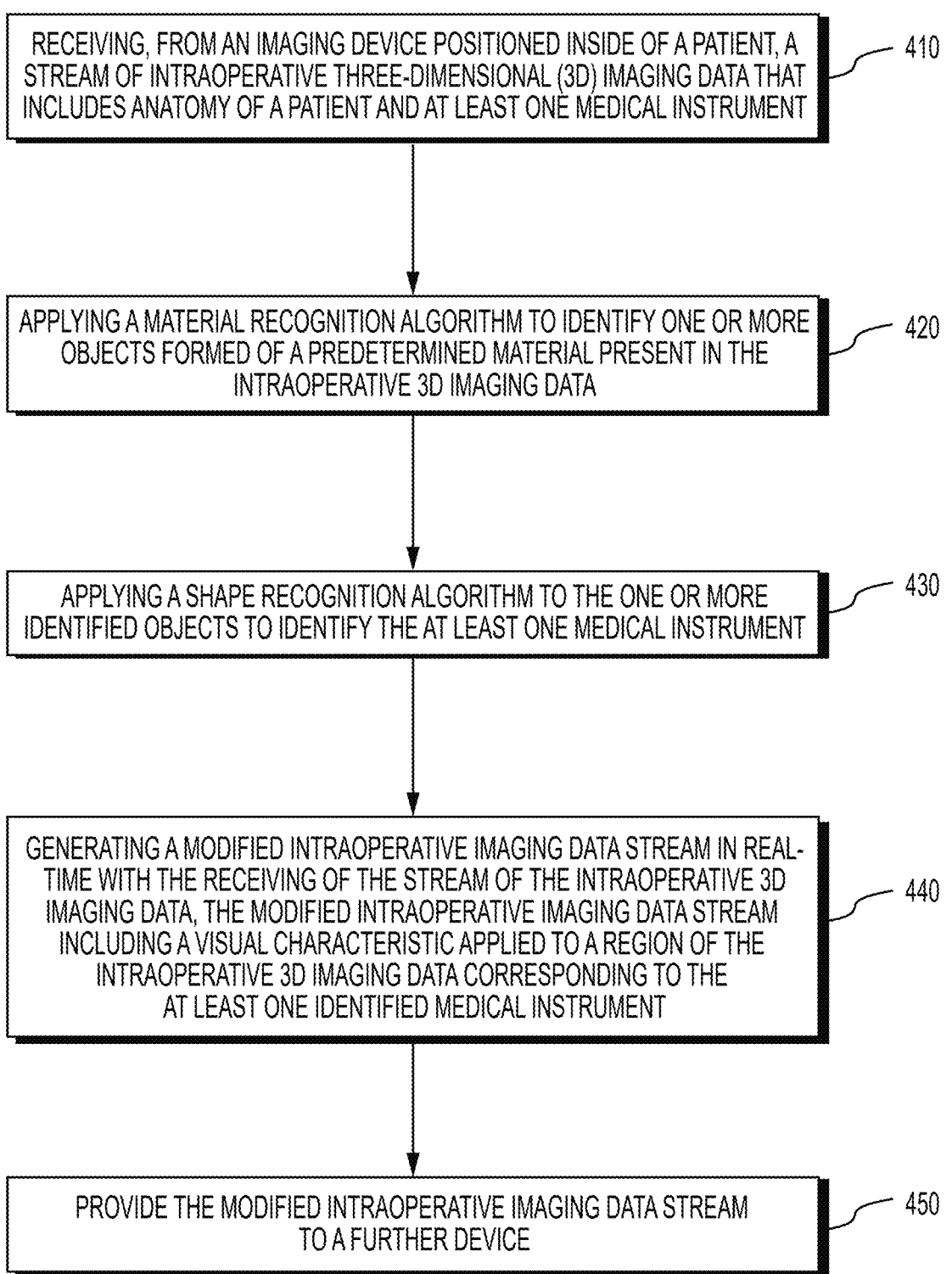

RECEIVING, FROM AN IMAGING DEVICE POSITIONED INSIDE OF A PATIENT, A STREAM OF INTRAOPERATIVE THREE-DIMENSIONAL (3D) IMAGING DATA THAT INCLUDES ANATOMY OF A PATIENT AND AT LEAST ONE MEDICAL INSTRUMENT — 410

APPLYING A MATERIAL RECOGNITION ALGORITHM TO IDENTIFY ONE OR MORE OBJECTS FORMED OF A PREDETERMINED MATERIAL PRESENT IN THE INTRAOPERATIVE 3D IMAGING DATA — 420

APPLYING A SHAPE RECOGNITION ALGORITHM TO THE ONE OR MORE IDENTIFIED OBJECTS TO IDENTIFY THE AT LEAST ONE MEDICAL INSTRUMENT — 430

GENERATING A MODIFIED INTRAOPERATIVE IMAGING DATA STREAM IN REAL-TIME WITH THE RECEIVING OF THE STREAM OF THE INTRAOPERATIVE 3D IMAGING DATA, THE MODIFIED INTRAOPERATIVE IMAGING DATA STREAM INCLUDING A VISUAL CHARACTERISTIC APPLIED TO A REGION OF THE INTRAOPERATIVE 3D IMAGING DATA CORRESPONDING TO THE AT LEAST ONE IDENTIFIED MEDICAL INSTRUMENT — 440

PROVIDE THE MODIFIED INTRAOPERATIVE IMAGING DATA STREAM TO A FURTHER DEVICE — 450

*FIG. 4*

COLORIZATION OF MEDICAL DEVICES IN ROBOTIC SURGERY USING AI AND MACHINE LEARNING

RELATED APPLICATIONS

This application claims priority to U.S. Provisional Application No. 63/711,850, filed Oct. 25, 2024, the entirety of which is incorporated herein.

TECHNICAL FIELD

Various embodiments of this disclosure relate generally to machine-learning-based techniques for object recognition during medical procedures, and, more particularly, to systems and methods for identifying one or more medical devices in a surgical imaging scene.

BACKGROUND

Medical procedures are often performed inside the body where the target and/or the instrument are hidden from the naked eye. Medical imaging is often used to provide imaging inside the body before, during or after such procedures, but it is often difficult to properly appreciate details in the imaging. In fact, depending on the circumstances, even seasoned professionals may improperly glean certain shadows or tones in the conventional imaging. Further, it remains difficult to ascertain certain imaging features, such as metal components and/or medical instruments. This may present patient safety issues and lead to injury or death. It may also prolong the length of a procedure as the physician or operator struggles to properly position instruments. The quality of the imaging may also lead to missing suspicious lesions or yielding false negative biopsies.

Conventional techniques, including the foregoing, fail to recognize, emphasize, or otherwise highlight certain objects routinely featured during medical imaging procures, including, but not limited to, bodily features and medical instruments, and portions thereof. This disclosure is directed to addressing challenges such as one or more of those referenced above. The background description provided herein is for the purpose of generally presenting the context of the disclosure. Unless otherwise indicated herein, the materials described in this section are not prior art in this application and are not admitted to be prior art, or suggestions of the prior art, by inclusion in this section.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, illustrate various exemplary embodiments and together with the description, serve to explain the principles of the disclosed embodiments.

FIG. 4 is a flowchart illustrating an exemplary method for intraoperative medical instrument recognition, according to aspects of the present disclosure.

SUMMARY

Figure 1:
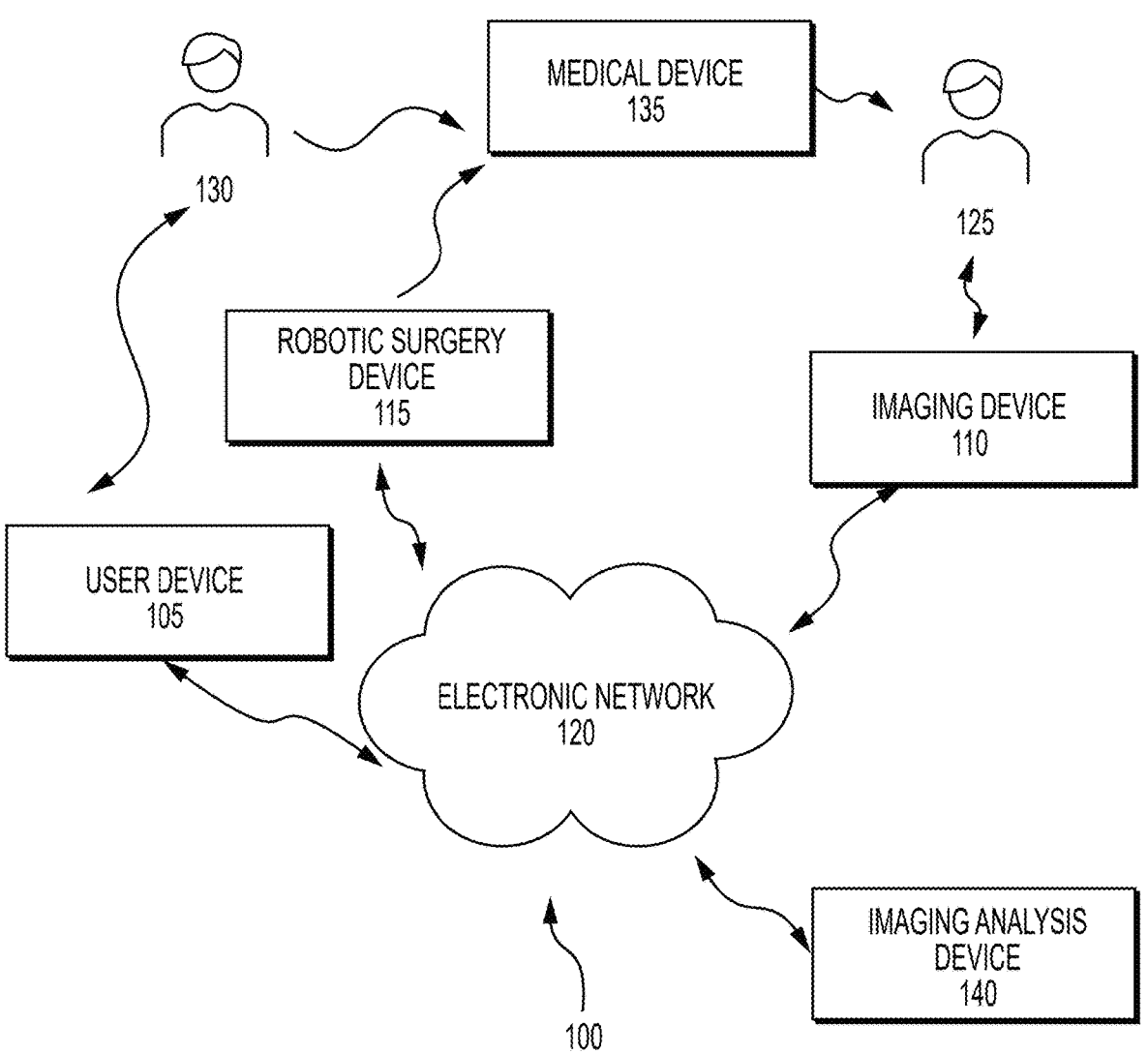
FIG. 1 depicts an exemplary environment for intraoperative medical instrument recognition, according to aspects of the present disclosure.

In some aspects, the techniques described herein relate to a computer-implemented method for intraoperative medical instrument recognition, the computer-implemented method including: receiving, from an imaging device positioned inside of a patient, a stream of intraoperative three-dimensional (3D) imaging data that includes anatomy of a patient and at least one medical instrument; applying a material recognition algorithm to identify one or more objects formed of a predetermined material present in the intraoperative 3D imaging data; applying a shape recognition algorithm to the one or more identified objects to identify the at least one medical instrument; and generating a modified intraoperative imaging data stream in real-time with the receiving of the stream of intraoperative 3D imaging data, wherein the modified intraoperative imaging data stream includes a visual characteristic applied to a region of the intraoperative 3D imaging data corresponding to the at least one identified medical instrument.

In some aspects, the techniques described herein relate to a computer-implemented method for object recognition during a medical procedure, including: receiving, from an imaging device positioned inside of a patient, an imaging scene of a target, the imaging scene including a medical instrument; applying a metal recognition algorithm to identify metal present in the imaging scene; applying an object recognition algorithm to the identified metal to identify the medical instrument; and generating a modified imaging scene that includes a visual characteristic applied to the identified medical instrument.

In some aspects, the techniques described herein relate to a system for intraoperative medical instrument recognition, including: at least one medical instrument; at least one imaging device configured to capture intraoperative three-dimensional (3D) imaging data; and an imaging analysis device that includes: at least one memory storing: instructions for intraoperative medical instrument recognition; a first machine-learning model that has been trained to identify at least one material included in the at least one medical instrument based on input imaging data, and to segment or generate a reconstruction of a shape of the identified at least one material in the imaging data; and a second machine-learning device that has been trained to recognize the at least one medical instrument based on an input shape; and at least one processor operatively connected to the at least one memory and configured to execute the instructions to perform operations including: receiving, from the imaging device, a stream of intraoperative 3D imaging data that includes anatomy of a patient and at least one medical instrument at least partially inserted into the anatomy; applying the first machine-learning model to the intraoperative 3D imaging data to identify one or more regions of the intraoperative 3D imaging data that include the at least one material, and to segment or generate a shape of the at least one material; applying the second machine-learning model to the shape to identify the at least one medical instrument; and generating a modified intraoperative imaging data stream in real-time with the receiving of the stream of intraoperative 3D imaging data, wherein the modified intraoperative imaging data stream includes a visual characteristic applied to a region of the intraoperative 3D imaging data corresponding to the at least one identified medical instrument.

DETAILED DESCRIPTION OF EMBODIMENTS

According to certain aspects of the disclosure, methods and systems are disclosed for object analysis and recognition during medical procedures, e.g. surgical imaging (including videos and images). It remains difficult to ascertain certain imaging features, such as metal components and/or medical instruments. This may present patient safety issues and lead to injury or death. However, conventional techniques may not be suitable. For example, conventional techniques may not adequately identify and indicate (or otherwise highlight and/or emphasize) certain objects/elements (and characteristics thereof) within an imaging scene. Accordingly, improvements in technology relating to object analysis, object recognition, and corresponding user interface elements are needed.

The systems, devices, and methods may apply artificial intelligence and/or machine learning techniques to enhance medical imaging object recognition. The exemplary embodiments may be used by a system to perceive one or more physical characteristics of surgical devices from images, video, and other media (including 3D formats). The systems, devices, and methods of the disclosure may be applied preoperatively to existing media (e.g., for training or review purposes), intraoperatively (e.g., to assist during a medical procedure), and/or post-operatively (e.g., for training or review purposes). The systems, devices, and methods may be used by humans and/or robotic surgical systems. In an example, a robotic surgical system may apply object recognition techniques described herein to improve its own surgical capabilities.

As will be discussed in more detail below, in various embodiments, systems and methods are described for using machine learning to improve object recognition during medical procedures. By training a machine-learning model, e.g., via supervised or semi-supervised learning, to learn associations between training data and ground truth data, the trained machine-learning model may be usable to identify and analyze objects in a medical imaging scene. It should be understood that the term "scene" as used herein may refer to a given field of view of a medical imaging device, such as a camera probe. Reference to an object being in a given scene should therefore be understood to mean that the field of view of the medical imaging device includes at least a portion of the given object.

Reference to any particular activity is provided in this disclosure only for convenience and not intended to limit the disclosure. A person of ordinary skill in the art would recognize that the concepts underlying the disclosed devices and methods may be utilized in any suitable activity. The disclosure may be understood with reference to the following description and the appended drawings, wherein like elements are referred to with the same reference numerals.

The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features, as claimed.

In this disclosure, the term "based on" means "based at least in part on." The singular forms "a," "an," and "the" include plural referents unless the context dictates otherwise. The term "exemplary" is used in the sense of "example" rather than "ideal." The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. The term "or" is used disjunctively, such that "at least one of A or B" includes, (A), (B), (A and A), (A and B), etc. Relative terms, such as, "substantially," "approximately," "about," and "generally," are used to indicate a possible variation of ±10% of a stated or understood value.

It will also be understood that, although the terms first, second, third, etc. are, in some instances, used herein to describe various elements, these elements should not be limited by these terms. These terms are only used to distinguish one element from another. For example, a first contact could be termed a second contact, and, similarly, a second contact could be termed a first contact, without departing from the scope of the various described embodiments. The first contact and the second contact are both contacts, but they are not the same contact.

As used herein, the term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

As used herein, a "machine-learning model" generally encompasses instructions, data, or a model configured to receive input, and apply one or more of a weight, bias, classification, or analysis on the input to generate an output. The output may include, for example, a classification of the input, an analysis based on the input, a design, process, prediction, or recommendation associated with the input, or any other suitable type of output. A machine-learning model is generally trained using training data, e.g., experiential data or samples of input data, which are fed into the model in order to establish, tune, or modify one or more aspects of the model, e.g., the weights, biases, criteria for forming classifications or clusters, or the like. Aspects of a machine-learning model may operate on an input linearly, in parallel, via a network (e.g., a neural network), or via any suitable configuration. By virtue of such training, a machine-learning model is converted from an un-trained and un-specific model to a model that is unique to and specifically configured for the particular purpose for which it is trained. In an example, training of a machine-learning model is analogous to a method of production in which the article produced is the trained model having unique characteristics by virtue of its particular training. Moreover, the result of training a machine-learning model using particular training data and for a particular purpose results in a technical solution to an inherently technical problem.

The execution of the machine-learning model may include deployment of one or more machine learning techniques, such as linear regression, logistical regression, random forest, gradient boosted machine (GBM), deep learning, or a deep neural network. Supervised or unsupervised training may be employed. For example, supervised learning may include providing training data and labels corresponding to the training data, e.g., as ground truth. Unsupervised approaches may include clustering, classification or the like. K-means clustering or K-Nearest Neighbors may also be used, which may be supervised or unsupervised. Combinations of K-Nearest Neighbors and an unsupervised cluster technique may also be used. Any suitable type of training may be used, e.g., stochastic, gradient boosted, random seeded, recursive, epoch or batch-based, etc.

In an exemplary use case, a trained machine model may be used by the exemplary systems, devices, and methods disclosed herein to identify and analyze one or more medical imaging scenes. During (or after) a medical procedure, an object recognition algorithm may be used to identify one or more objects in a medical imaging scene. Such identification may be used for various purposes. In one example, the identification may be used to augment a display of the one or more identified objects on an adjustable graphic user interface (GUI). In another example, the identification may be used to guide or augment the operation of a robotic surgery device, e.g., by locating an implement wielded by the surgery device within the body of a patient, by locating anatomy, or the like.

In another exemplary use case, a machine-learning model may be trained to identify one or more characteristics of an identified object. For example, an object recognition algorithm of the systems, devices, and methods of the disclosure may identify that a given object in a scene is a medical instrument. The algorithm may further identify that the given object is of a certain material (e.g., metal), is of a certain size (e.g., dimensional measurements), how or how much of an object is occluded from view, and/or whether the object is of a certain color. Any recognized object and characteristic(s) thereof may be displayed on a GUI that may be adjustable by a user. Further description of the GUI is provided below.

While several of the examples above involve medical imaging, it should be understood that techniques according to this disclosure may be adapted to any suitable type of imaging. It should also be understood that the examples above are illustrative only. The techniques and technologies of this disclosure may be adapted to any suitable activity.

Presented below are various aspects of machine learning techniques that may be adapted to recognize, identify, and/or characterize one or more objects in a medical imaging scene. As will be discussed in more detail below, machine learning techniques adapted to medical imaging may include one or more aspects according to this disclosure, e.g., a particular selection of training data, a particular training process for the machine-learning model, operation of a particular device suitable for use with the trained machine-learning model, operation of the machine-learning model in conjunction with particular data, modification of such particular data by the machine-learning model, etc., or other aspects that may be apparent to one of ordinary skill in the art based on this disclosure.

FIG. 1 depicts an exemplary environment 100 according to one or more aspects of this disclosure. The environment 100 may include, for example, a user device 105, an imaging device 110, a robotic surgery device 115, which may communicate via an electronic network 120. A patient 125 may be the focus of a medical procedure associated with a provider 130. The medical procedure may include introduction of one or more medical devices 135 into the body of the patient 125. As discussed in further detail below, an imaging analysis device 140 may be configured to augment medical imaging data generated by the imaging device 110, e.g., by identifying the one or more medical devices 135, anatomy of the patient 125, and/or their relative location or other context.

The user device 105 may include a computer system such as a desktop computer, laptop computer, tablet computer, mobile phone, etc. The user device 105 may include software and/or hardware configured to communicate with or operate in conjunction with other elements of the environment 100. For example, the user device 105 may be configured to operate the robotic surgery device 115, display medical imaging from the imaging device 110, etc.

The imaging device 110 may be configured to capture any suitable type of medical imaging. In an exemplary embodiment, the imaging device 110 may include a Three-Dimensional (3D) video device, a 3D ultrasound device, or any other suitable type of 3D imaging device. The imaging device 110 may be configured to store imaging data in a memory, e.g., of the user device 105, a remote data storage, a cloud storage, or the like. In some embodiments, an imaging device 110 is integrated into a medical device 135. For example, an endoscope may be fitted with a camera or an ultrasound probe, or the like.

The robotic surgery device 115 may include one or more articulatable or robotically controlled arms or digits which may include or be fitted with one or more medical instruments. In some embodiments, the medical devices 135 are medical instruments integrated into or fitted onto the robotic surgery device 115. Examples of such medical instruments include, but are not limited to, graspers, scissors, needle holders or manipulators, suction or irrigation devices, drapes, endoscopes, medical imaging devices, clip appliers, energy devices (e.g., for powering another device such as a laser, cutter, etc.), a cauterizing device, a retractor, a bipolar or laser device, an EndoWrist®, etc. In various embodiments, the robotic surgery device 115 may be controllable, e.g., via the user device 105, and/or may be configured to execute preprogrammed operations.

In some embodiments, the robotic surgery device 115 may be configured to process medical imaging data, e.g., from the imaging device 110, in order to locate a medical device 135 and/or anatomy of the patient 125 and/or other context of a procedure. However, as discussed above, the capability of the robotic surgery device 115 to process medical imaging, like the capability of the provider 130 may be impacted by the difficulty of visualizing or detecting medical instruments in conventional medical imaging. According to one or more aspects of this disclosure, the augmented medical imaging provided by the imaging analysis device 140 may improve the efficiency, accuracy, or speed of the robotic surgery device 115. In some embodiments, however, a robotic surgery device may not be used. For example, the provider 130 may directly manipulate a medical device 135 within the body of the patient 125.

The electronic network 120 may be wired, wireless, or a combination thereof. Such network may be a local or personal network, or may include a connection via the internet. In some embodiments, the electronic network 120 may include or be in communication with an Electronic Medical System (EMS), e.g., a data system at a hospital or the like used to store and communicate patient data and the like.

In some embodiments, other sensors (not shown) may be used to monitor various characteristics of the patient 125, e.g., blood pressure, temperature, neural activity, etc., In some embodiments, such data may be fed to the user device 105, the robotic surgery device 115, the imaging analysis device 140, or the like, which may use such data as additional input when processing imaging data and or guiding use of or operating a medical device 135.

As noted above, in some embodiments, the medical device 135 may be integrated into or affixed onto the robotic surgery device 115. In some embodiments, the robotic surgery device 115, e.g., via use of such a medical device, is operated to manipulate a further medical device. For example, a needle holder may be used to hold or manipulate a needle. Other examples of medical devices 135 include, but are not limited to, a needle assembly, tubular members, needles, trocars, cutting styli, styli, cannula, and/or other components configured to access and sever a tissue sample in a medical procedure commonly referred to as Core Needle Biopsy. However, the foregoing examples are exemplary only, and any suitable medical devices 135 may be used.

As discussed in further detail below, the imaging analysis device 140 may include one or more models or algorithms usable to process imaging data and apply a visual characteristic to medical devices 135 identified therein. In an example, the imaging analysis device 140 may include one or more trained machine-learning models. In an embodiment, a first machine-learning model may have been trained to identify matter in medical imaging that is formed from a particular material, e.g., metal. Further, such model may be configured to segment the identified material, e.g., determine shape or geometry information for the identified material. A second machine-learning model may have been trained to recognize one or more medical devices given a shape or geometry, such as the shape or geometry determined by the first machine-learning model.

In embodiments, the first and/or second machine-learning models may be trained based at least in part on imaging of medical devices 135 within anatomy of one or more patients. In some embodiments, the first and/or second machine-learning models may be trained on a stream or sequence of imaging frames or states. Such training may facilitate identification and recognition operations when a medical device is moving, is partially occluded, is changing shape during operation, or is interacting with anatomy.

As discussed in further detail below, the imaging analysis device 140 may perform one or more of generating, storing, training, or using a machine-learning model configured to recognize and identify objects in a medical imaging scene. The imaging analysis device 140 may include a machine-learning model or instructions associated with the machine-learning model, e.g., instructions for generating a machine-learning model, training the machine-learning model, using the machine-learning model etc. The imaging analysis device 140 may include instructions for retrieving imaging data, adjusting imaging data, e.g., based on the output of the machine-learning model, or operating the user device 105 to output modified imaging data, e.g., as adjusted based on the machine-learning model. The imaging analysis device 140 may include training data, e.g., teaching data, and may include ground truth, e.g., evaluative data.

In some embodiments, a system or device other than imaging analysis device 140 is used to generate or train the machine-learning model. For example, such a system may include instructions for generating the machine-learning model, the training data and ground truth, or instructions for training the machine-learning model. A resulting trained-machine-learning model may then be provided to imaging analysis device 140.

Generally, a machine-learning model includes a set of variables, e.g., nodes, neurons, filters, etc., that are tuned, e.g., weighted or biased, to different values via the application of training data. In supervised learning, e.g., where a ground truth is known for the training data provided, training may proceed by feeding a sample of training data into a model with variables set at initialized values, e.g., at random, based on Gaussian noise, a pre-trained model, or the like. The output may be compared with the ground truth to determine an error, which may then be back-propagated through the model to adjust the values of the variable. In unsupervised learning, patterns, correlations, or clusters of input samples may be used to determine one or more metrics or features of the samples usable to differentiate between related subsets of the samples. In semi-supervised learning, unsupervised and supervised approaches may be combined.

Training may be conducted in any suitable manner, e.g., in batches, and may include any suitable training methodology, e.g., stochastic or non-stochastic gradient descent, gradient boosting, random forest, etc. In some embodiments, a portion of the training data may be withheld during training or used to validate the trained machine-learning model, e.g., compare the output of the trained model with the ground truth for that portion of the training data to evaluate an accuracy of the trained model. The training of the machine-learning model may be configured to cause the machine-learning model to learn associations between training data and ground truth data, such that the trained machine-learning model is configured to determine an output (e.g., an identified object in a medical imaging scene) in response to the input medical imaging data based on the learned associations. Particular selection or application of training data, such as discussed in various embodiments of this disclosure, may inhibit or reduce impact of concerns such as biasing (e.g., via selection, truncation, or the like), overfitting, under-fitting, etc.

In some instances, training using one set or type of data may be used or adapted to another set of data. For example, a modal initially trained on one data set may require less samples or time to train on a second data set. In another example, initial training may result in a base model that may be tuned with an additional data set so as to form a particularized model specific to circumstances of the additional data set.

In various embodiments, the variables of a machine-learning model may be interrelated in any suitable arrangement in order to generate the output. For example, in some embodiments, the machine-learning model may include image-processing architecture that is configured to identify, isolate, or extract features, geometry, and or structure in one or more of the medical imaging data or the non-optical in vivo image data. For example, the machine-learning model may include one or more convolutional neural network ("CNN") configured to identify features in the medical imaging data, and may include further architecture, e.g., a connected layer, neural network, etc., configured to determine a relationship between the identified features in order to determine a label and/or characteristic of the identified object.

In some instances, different samples of training data or input data may not be independent. Thus, in some embodiments, the machine-learning model may be configured to account for or determine relationships between multiple samples.

For example, in some embodiments, the machine-learning model of the imaging analysis device 140 may include a Recurrent Neural Network ("RNN"). Generally, RNNs are a class of feed-forward neural networks that may be well adapted to processing a sequence of inputs. In some embodiments, the machine-learning model may include a Long Short Term Memory ("LSTM") model or Sequence to Sequence ("Seq2Seq") model. An LSTM model may be configured to generate an output from a sample that takes at least some previous samples or outputs into account. A Seq2Seq model may be configured to, for example, receive a sequence of optical in vivo images as input, and generate a sequence of labels and/or characteristics, in the medical imaging data as output.

Various features may be included or used with any suitable machine learning model. For instance, a model may be configured to receive and or determine a relative positioning of data or portions of data in samples (e.g., location of pixels in an image, etc.), and use such positions as a portion of the input to the model. In another instance, a model configured to utilize attention may be configured to weigh, determine, or the like how different samples or portions of samples impact the output of the model, and may incorporate such data into the training process. An example of a model that utilizes information on relative positioning and attention is a transformer model. One implementation incorporating a transformer is a large language model. Transformers and other suitable models have been used for multi-modal input, e.g., a model that is configured to use and process input of different modalities (a combination of or selection from one or more of text, audio, video, structured or unstructured data, etc.).

Any suitable type of machine learning model or combination of machine learning models may be used. Operations conducted by one model in some embodiments may be distributed amongst a plurality of models in other embodiments, or vice versa.

Certain elements of the environment 100 may have been referred to as distinct devices. However, it should be understood that, in various embodiments, various elements may have one or more components distributed over one or more devices or in one or more locations. In an example, a user device 105 may include a client device proximal to the patient 125 and a server device at a remote location.

In the following systems, devices, and methods, various acts may be described as performed or executed by a component from FIG. 1, such as the imaging analysis device 140 or components thereof. However, it should be understood that in various embodiments, various components of the environment 100 discussed above may execute instructions or perform acts including the acts discussed below. An act performed by a system or device may be considered to be performed by a processor, actuator, or the like associated with that system or device. Further, it should be understood that in various embodiments, various steps may be added, omitted, or rearranged in any suitable manner.

In an exemplary use case, a provider 130 may seek to perform a procedure on a patient 125. The imaging device 110 may be used prior to the procedure, e.g., for planning or review purposes, as well as during the procedure to facilitate the manipulation of one or more medical devices 135.

For example, during a procedure, the imaging device 110 may be capturing imaging data of the anatomy of the patient, e.g., 3D ultrasound imaging. In various examples, a medical device 135 may be advanced to a location within the body through the skin of the patient 125 (percutaneous access), through an open incision or through a body lumen or other structure, a portion of the medical device 135 may be advanced into a lesion or target tissue, or a portion of the medical device 135 may be advanced into the lesion or target tissue to sever a tissue sample from the lesion or target tissue. In some examples, the medical device 135 may be manipulated by the provider 130. In some examples, the medical device 135 may be manipulated by the robotic surgery device 115.

During the procedure, the imaging device 110 may be capturing imaging data of the anatomy of the patient, e.g., a scene that includes at least a portion of the medical device 135. In an example, the imaging device 110 may include an imaging probe inserted into the body of the patient alongside or as part of the medical device 135. In another example, the imaging device may be operated externally to the body of the patient. Any suitable type or combination of types of imaging devices may be used.

Imaging data captured by the imaging device 110 may be fed to the imaging analysis device 140, e.g., as a data stream or the like. The imaging analysis device 140 may process the imaging data, e.g., via one or more machine-learning models, in order to identify the medical device 135 and apply a visual characteristic to it. In an example, the visual characteristic may include a colorization. For instance, different medical devices may have predetermined associations with different colorings, and so a particular coloring may be applied to the portion of a display of the imaging device corresponding the identified medical device 135.

In some embodiments, the object recognition by the imaging analysis device 140 may include the use of multiple machine-learning models. For instance, a first model may have been trained to recognize one or more different materials. Generally, medical devices to be inserted into the body of a patient are formed from biocompatible materials that are distinguishable from body tissue under various types of medical imaging. In optical video, for example, metal generally has a shiny or reflective appearance. In ultrasound imaging, for example, different materials have different echogenic responses based on their density and acoustic properties. The first model may have been trained based on labeled imaging data of different materials viewed under one or more imaging modalities, e.g., in situ within anatomy of a body. Thus, the first model may be trained to identify portions of a scene that include a particular material.

In some instances, the first model may identify a shape of identified material. For example, the first model may identify multiple pixels or voxels that are likely to include a certain material, and then may perform a segmentation process or the like to determine a shape of an object that includes those pixels or voxels. The identified shape may be two-dimensional or three-dimensional. In some cases, two-dimensional imaging data may be usable via the first model to predict or extrapolate a three-dimensional shape of an object. For instance, the first model may be trained using predetermined shapes within various anatomy, and thus may have learned to predict a three-dimensional shape of an object given the context of surrounding anatomy. In some cases, the imaging data may be 3D imaging data, whereby a 3D shape may be determined via segmentation or the like directly.

A second model may be used to recognize which medical device an identified shape corresponds to. For example, the second model may have been trained based on training shape data labeled with associated medical devices. In some embodiments, the first model may be used to generate training data for the second. For example, the first model may be used to generate shape data for known medical devices in various positions and in various contexts, whereby such shaped data may be used along with labels regarding the known medical devices to train the second model.

Such identification and recognition may occur continuously during the procedure. Further, the application of the visual characteristic, e.g., the colorization, may be continuously updated, such that the medical device 135 is colored as it moves or is reoriented, e.g., even if a portion is occluded or moves out of the scene. In some instances, the recognition via the second model includes determination of an orientation or path of motion of the medical device 135. For example, by accounting for the position or motion of the recognized medical device 135 over time (e.g., across frames of the imaging data), the second model may be configured to account for occlusions or changes in perspective of the medical device 135.

Further, such operations may be performed for multiple medical devices 135 in the scene, e.g., such that medical devices that might otherwise be hard to distinguish from each other may be clearly disambiguated visually.

In some instances, the modified imaging data, e.g., that includes colorizations, may be output on the user device 105. This may enable a provider 130 to clearly apprehend the state and position of such devices within the body of the patient 125. In some instances, the modified imaging data is fed to the robotic surgery device 115, which may be configured to use the applied visual characteristic to determine the position, orientation, or status of the medical device 135 relative to the anatomy of the patient 125.

The visual characteristics may enable the provider 130 and/or the robotic surgery device 115 to more accurately apprehend the position and state of the medical device 135 and the anatomy of the patient 125, and thus may enable a more accurate and faster completion of the procedure, which may improve patient outcomes. In an example where the procedure includes performing a biopsy, the imaging analysis device 140 may enable more accurate engagement with a biopsy site, leading to a reduction in inaccurate biopsy sampling.

Once the procedure is completed, the medical device 135 may then be withdrawn from the patient 125 and, for example, a tissue sample extracted from a needle assembly may be taken for analysis.

Further aspects of the machine-learning model or how it may be utilized to recognize and identify objects and characteristics thereof are discussed in further detail in the methods below.

Figure 2A:
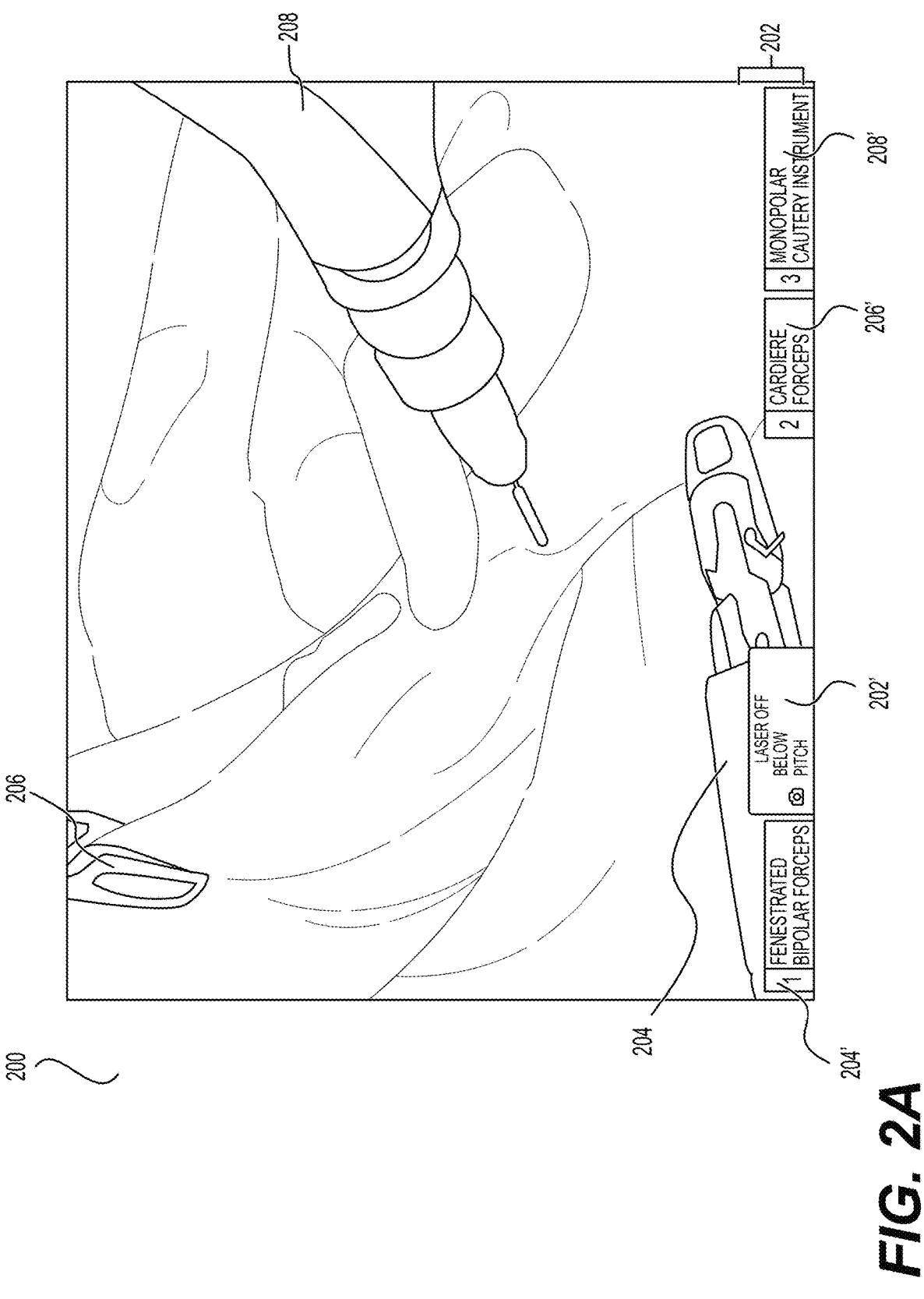
FIGS. 2A-2B are photographs showing a first target site without and with annotation, according to aspects of the present disclosure.
Figure 2B:
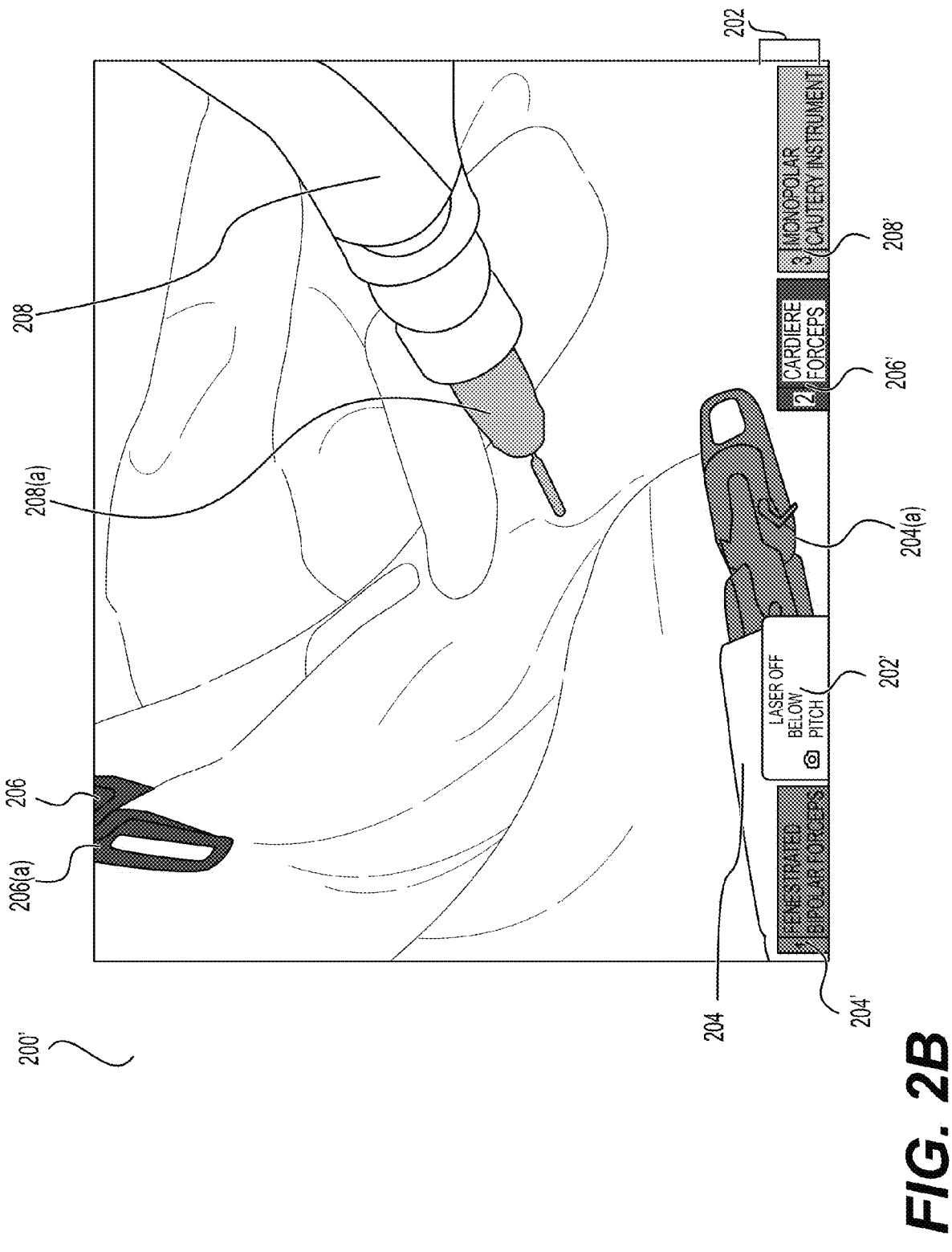

FIGS. 2A-2B are exemplary imaging scenes showing a first target site without and with application of visual characteristics to medical devices, according to aspects of the present disclosure. In an example, an imaging scene 200 is shown in FIG. 2A, without labeling/highlighting/annotations. The same imaging scene is shown in FIG. 2B, but is denoted with reference numeral 200′ to indicate the presence of labeling/highlighting/annotations as applied by imaging analysis device 140. It should be further understood that the appearance of text labeling (e.g., hook) of an object is only for explanatory purposes of the disclosure. For example, a user may not see the word "hook" on the user interface element corresponding to hook 208, unless so desired (e.g., via a preference or user input). It will be appreciated that the images shown in FIGS. 2A-3B, 3A-3B may be displayed on the user device 105, along with a GUI including one or more user interface elements that may be adjusted or changed by imaging analysis device 140.

FIG. 2A shows an image taken during a medical procedure (e.g., a cholecystectomy) using imaging analysis device

140. The medical procedure may involve the use of one or more medical instruments 135 and an imaging device 110. The image may be a still photograph (including contemporaneous and/or prerecorded) or may be representative of a frame from a video feed (including contemporaneous and/or prerecorded). It will be appreciated that the systems, devices, and methods of the disclosure may be applicable to images and videos, both contemporaneous (e.g., live) and prerecorded. Also, while FIGS. 2A and 2B depict optical camera imaging, imaging may also be ultrasound, e.g., 3D ultrasound imaging, magnetic resonance imaging, Computed Tomography imaging, or any other suitable type of imaging. And as noted above, the term "scene" refers may refer to a given field of view of an imaging device 110. Reference to an object being in a given scene should therefore be understood to mean that the field of view of the medical imaging device includes at least a portion of the given object.

Imaging scene 200 may include one or more objects and/or elements. It will be appreciated that imaging analysis device 140 may be used with a variety of medical devices 135 and instruments for a variety of medical procedures. Accordingly, the medical function(s) of medical instruments noted below will not be discussed unless otherwise noted. Imaging scene 200 includes fenestrated forceps 204, cardiere forceps 206, and a hook 208, each of which may be used alone or in combination during the medical procedure.

It may be clinically valuable for imaging analysis device 140 to identify one or more material properties of the objects in an imaging scene. In particular, identification of metal may be important. It may be beneficial to identify which elements of a scene are metal as compared to tissue or plastic or other materials. It may be beneficial to identify foreign objects, such as metal fragments (for example, due to an instrument failure) or inadvertently left-behind metal objects (such as screws or staples). In some instances, contact between metal and certain medical devices (such as a cautery device) may cause complications or injury to a patient. Detection of metal may allow be beneficial to more readily adjust certain implants (e.g., a certain metal portion may need to be oriented in a certain position). Additionally, the presence of metal may be a significant indication of a presence of a medical implement. For example, a metal may exhibit distinct visual properties relative to a patient's anatomy, e.g., tissue. Thus, the presence and/or location of metal in a scene, as well as the shape of such detected metal, may be usable to identify one or more medical devices that may be present.

Imaging analysis device 140 may identify metal in an imaging scene. For example, imaging analysis device 140 may apply one or more trained object recognition models and/or algorithms to a given imaging scene to identify that metal is present and what type of object and/or instrument that metal corresponds to. In an example, imaging analysis device 140 may identify the metal portion of fenestrated forceps (shown in FIG. 2B at 204($a$)). Based on the identified portion of metal, imaging analysis device 140 may then determine what type of medical instrument (or other object, such as a metal fragment) corresponds to the given portion of identified metal (e.g., fenestrated forceps 204). It will be appreciated that imaging analysis device 140 may apply separate algorithms (e.g., a metal identification algorithm and then an object identification algorithm) or may apply a single algorithm including both metal identification/detection and object identification.

In an example, a metal detection algorithm or model may determine a likelihood that various regions of the imaging scene (e.g., each pixel, a sub-region, etc.) contains metal. In an example, the metal detection algorithm or model may generate a detected metal map, e.g., a value for each pixel in the image scene that is indicative of a presence or lack thereof of metal. In some embodiments, the value may be binary, e.g., either the likelihood of the presence of metal at a particular pixel is above a predetermined threshold or not. In some embodiments, the value may correspond to the likelihood, e.g., so that the map may be represented as a grayscale image depicting a heat-map for the presence of metal. In some embodiments, as noted above, the presence of metal may be evaluated for a sub-region of the scene, e.g., a cluster of pixels, a portion of the image scene, etc. In some embodiments, the image scene may be sub-divided, e.g., iteratively or in parallel or otherwise, into sub-portions of varying size. This may enable isolation of a region of the scene containing a medical implement of different sizes. In some embodiments, a preprocessing may be applied to the image scene prior to the metal detection. For instance, a smoothing or clustering of pixels may be performed such that, for example, only groupings of pixels above a predetermined size containing metal are evaluated.

In various embodiments, the metal detection algorithm or model may incorporate one or more machine-learning techniques. For example, the algorithm or model may be trained on one or more training scenes that include labelled regions containing metal. Example training data may include surgery image scenes that are labeled to identify metal, images of various metals under various lighting condition and/or in the presence of various anatomy or the like, etc. In an example, the algorithm or model may include a CNN, an RNN, or the like.

In an example, the object detection algorithm or model may receive and/or determine a shape of a portion of metal detected by the metal detection algorithm or model, and correlate the shape with a medical implement. For example, the object detection algorithm or model may match a shape with similar shapes of previously identified objects, e.g., using any suitable shape matching process. In another example, the object detection algorithm or model may employ one or more machine-learning techniques. For instance, the object detection algorithm or model may be trained using labeled shapes corresponding to medical implements from various angles and at various distances, resolutions, etc. In some instances, the object detection algorithm or model may be further configured to determine an orientation and/or direction of motion of an object. For example, a two-dimensional shape of a region of metal, e.g., from the map above, may be correlated with a three-dimensional model of a particular object at a particular orientation. In other words, the shape of the metal region may be usable to determine an orientation of the identified object.

In another example, information from multiple image scenes over time may be used to determine information about an object. For instance, different portions of an object may be visible at different times, and one or more of the metal detection or object detection algorithm or model may be configured to track locations of metal or identified objects over time, e.g., to maintain tracking or identification of an object even though a portion of the object moves out of the scene or is obstructed. In another instance, the tracking may be used to determine a path of motion and/or a predicted motion or position at a future instance of time.

An approach incorporating one or more of the techniques above may result in various technical improvements for detection of medical implements in a surgery image scene.

For example, by isolating portions, e.g., pixels, of an image scene having a particular material such as metal prior to performing object identification, a system may reduce the amount of data that needs to be analyzed to perform the identification, may reduce the complexity or computing cost of the algorithms or models employed, or may improve the accuracy of results. In an example, a system incorporating one or more of the techniques above may be configured to provide identification and highlighting of medical implements in real or near-real time, e.g., as a live overlay on imaging output during a surgery or procedure.

It will be appreciated that while discussion above relates to metal, imaging analysis device 140 may identify other materials and corresponding objects as well (e.g., glass, plastic, ceramics, etc.).

In an example, the shape of a portion of metal identified as a medical implement or the like may be used to generate a graphical overlay, highlight, or the like. For example, a partially transparent shape corresponding to an identified portion of metal may be generated to visually identify a medical implement, and then overlaid on the imaging scene, e.g., in real or near-real time. In some instances, a plurality of objects may be identified in this manner. In some instances, an interface, an overlay, or the like may include a text identification of an object and/or a legend correlating a particular color to a particular object. In some instances, a highlight, legend, graphical object, or the like may be generated to indicate other information about a medical implement, e.g., an orientation, a path of motion, a predicted trajectory, etc. Further, it should be understood that the foregoing examples are illustrative only, and that any suitable labeling or highlighting technique may be used.

In a particular example, imaging scene 200 may include a GUI 202. GUI 202 may include one or more user interface elements corresponding to one or more objects in an imaging scene (e.g., imaging scene 200). GUI 202 may be in any suitable position and take any suitable form as displayed by user device 105, as the GUI shown in FIG. 2A is only exemplary. In some aspects, GUI 202 may be toggled on or off in an unlabeled view (e.g., corresponding to FIG. 2A). In an example, GUI 202 may include a user interface element 204', which may correspond to fenestrated forceps 204. In the exemplary FIG. 2A, user interface elements corresponding to objects in imaging scene 200 are provided with a number (e.g., 1) and a label (e.g., fenestrated bipolar forceps). It should be noted that the number and label may be used alone or in combination with any other suitable user interface element, which will be discussed in greater detail below.

GUI 202 may include a user interface element 204' (corresponding to fenestrated forceps 204), a user interface element 206' (corresponding to cadiere forceps 206), and a user interface element 208' (corresponding to hook 208 (e.g., a monopolar cautery instrument)). GUI 202 may also include a user interface element 202' which may include various data related to the current imaging device 110 including but not limited to, pitch, roll, yaw, Cartesian and/or polar coordinates relative to a known reference point, magnification, directionality (e.g., which direction is up/down), shutter speed, scale (e.g., a reference as to the approximate size of objects in the imaging scene), ISO, aperture, color space, lighting controls (including intensity, white balance, hue, shade, and tint), lighting spectrum (e.g., visible, UV, IR, etc.) and any other suitable photographic/video graphic metric.

FIG. 2B shows imaging scene 200' which may be substantially similar to imaging scene 200, except with the addition of highlighting/labeling as provided by imaging analysis device 140 having performed object recognition of imaging scene 200. For example, a user may cause imaging analysis device 140 to activate a "highlight" mode/function of the imaging scene 200, such that imaging analysis device 140 performs object recognition and alters what is shown on user device 105 based on the object recognition. Imaging analysis device 140 may adapt, modify, or otherwise change GUI 202 and any of its corresponding user interface elements when identifying/highlighting objects in the imaging frame.

As shown in FIG. 2B, imaging analysis device 140 may recognize the various medical instruments in the imaging frame and may apply one or more visual characteristics or user interface elements to the identified objects. In the example of FIG. 2B, this may take the form of colored highlighting (e.g., a given medical instrument has a color/shading applied such that user device 105 shows the medical instrument with the given color applied). This is only exemplary, however, and other means of highlighting, emphasizing, or otherwise identifying an object in a scene may be used. For example, imaging analysis device 140 may use text (e.g., labeling), bounding boxes, blurring of background elements, highlighting with shadows or glow, magnification, pulsation/animation, changing of textures or patterns, convert the background to grayscale, apply a depth-of-field effect, applying one or more overlays, adding 3D effects/shadowing, labeling with icons, and/or radial highlighting (e.g., pointing arrows). Any of the aforementioned techniques may be applied alone or in combination with any other technique, and any of the aforementioned techniques may be selectively toggled by a user (e.g., via imaging analysis device 140). The aforementioned techniques may also be referred to as visual characteristics.

In the example of FIG. 2B, forceps 204, cardiere 206, and hook 208 may each have an overlay color applied (green, blue, and teal, respectively). The green highlight applied to fenestrated forceps 204 is indicated by highlight 204 (*a*), the blue highlight applied to cardiere forceps 206 is indicated by highlight 206 (*a*), and the teal highlight applied to hook 208 is indicated by highlight 208 (*a*). GUI 202 may also include the corresponding coloring applied to user interface element 204' (corresponding to fenestrated forceps 204), user interface element 206' (corresponding to cadiere forceps 206), and a user interface element 208' (corresponding to hook 208 (e.g., a monopolar cautery instrument)).

Figure 3A:
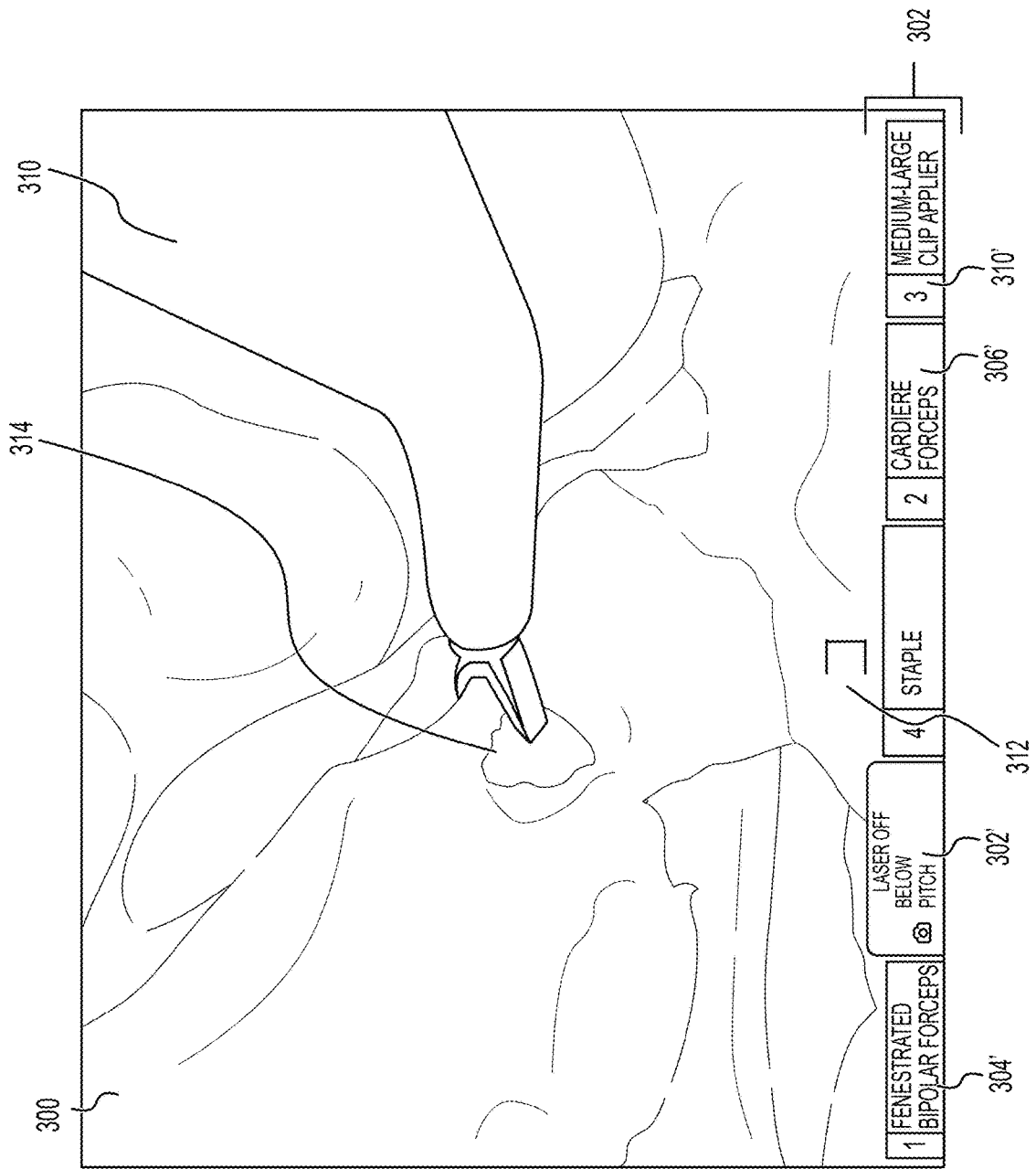
FIGS. 3A-3B are photographs showing a first target site without and with annotation, according to aspects of the present disclosure.
Figure 3B:
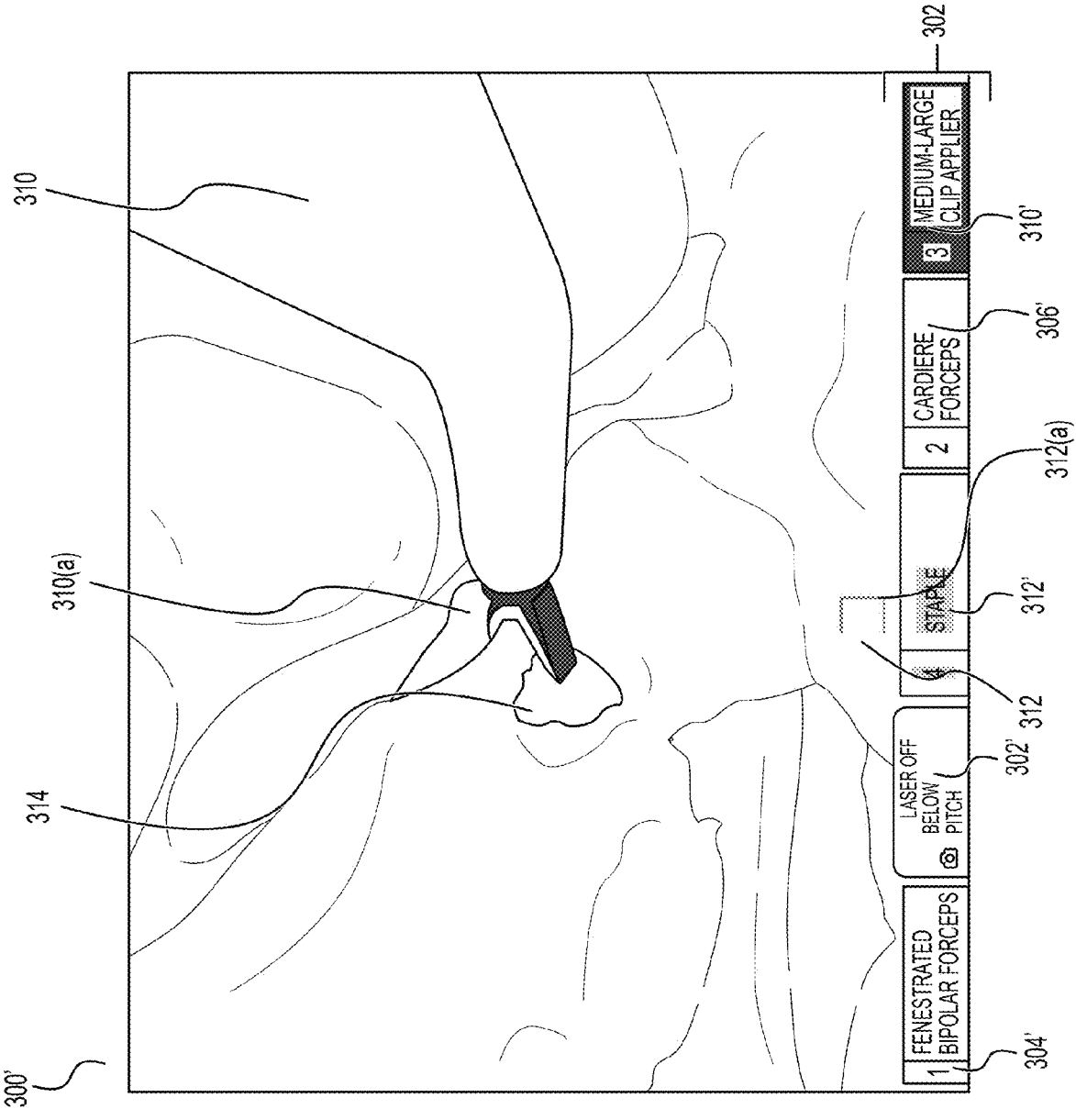

FIGS. 3A-3B are imaging scenes, showing an imaging scene 300 without and with annotation, according to aspects of the present disclosure. Imaging scene 300 may include similar instruments and GUI as FIG. 2A-2B, as indicated by like reference numerals. Of note in FIG. 3A is the addition of medical instruments including staple 312 (and a corresponding user interface element 312') and a clip (e.g., staple) applier 310 (and a corresponding user interface element 310'). Additionally shown in FIG. 3A is a target 314, which may be a portion of tissue that may be included as part of a medical procedure. Thus, in some aspects, imaging analysis device 140 may apply object recognition of anatomy, such as target 314. FIG. 3B shows imaging scene 300', showing imaging scene 300 with highlighting (or other visual characteristics) applied. As shown in FIG. 3B, the green highlight applied to staple 312 is indicated by highlight by highlight 312 (*a*), and the blue highlighting may be applied to a metallic portion of clip applier 310, indicated by highlight 310 (*a*). In the example of FIG. 3B, imaging analysis device 140 may be instructed to highlight (or apply any aforementioned visual characteristic) to objects in the imaging scene. For example, a user may indicate that all metallic objects in the imaging scene 300 should be highlighted. Thus, imaging analysis device 140 may apply highlighting to staple 312 and the metallic portion of clip applier 310.

FIG. 4 is a flowchart of an example method for intraoperative medical instrument recognition. A provider 130 may seek to perform a procedure on a patient 125. The provider 130 may employ one or more medical instruments 135 during the procedure, and may utilize one or more imaging devices 110 to image an inside of the body of the patient during the procedure. One or more of the medical instruments 135 may be at least partially inserted into the body of the patient, and the medical imaging device 110 may be operated so as to image a portion of the body of the patient 125 such that the portion of the medical instrument is within the scene generated by the imaging device 110.

At step 410, an imaging analysis device 140 may receive, from the imaging device 110, a stream of intraoperative three-dimensional (3D) imaging data that includes anatomy of a patient 125 and the at least one medical instrument 135. In some embodiments, the imaging data includes 3D ultrasound imaging data. In some embodiments, the imaging data includes 3D video.

At step 420, the imaging analysis device 140 may apply a material recognition algorithm to identify one or more objects formed of a predetermined material present in the intraoperative 3D imaging data, e.g., the scene generated by the imaging device 110. In some embodiments, the material recognition algorithm is configured to determine a likelihood that pixels or voxels of the imaging data includes the predetermined material. In some embodiments, the algorithm is configured to generate a material map indicative of locations or shapes of the predetermined material within the scene. The predetermined material may be metal. The material recognition algorithm may include executing a trained machine-learning model configured to identify portions of the predetermined material in a scene and to segment or reconstruct a shape (e.g., an object) of the predetermined material in the scene.

At step 430, the imaging analysis device 140 may apply a shape recognition algorithm to the one or more identified objects to identify the at least one medical instrument 135. In some embodiments, the shape recognition algorithm may include executing a trained machine-learning model configured to recognize medical instruments based on input shape or object data.

At step 440, the imaging analysis device 140 may generate a modified intraoperative imaging data stream in real-time with the receiving of the stream of intraoperative 3D imaging data. The modified intraoperative imaging data stream may include a visual characteristic applied to a region of the intraoperative 3D imaging data corresponding to the at least one identified medical instrument 135. The visual characteristic may include, for example, a colorization, an outline, a highlight, a text label, or the like.

At step 450, the modified intraoperative imaging data stream may be provided to a further device. In some embodiments, the further device may include a user device 105 to display the modified intraoperative imaging data stream to the provider 130. In some embodiments, the further device may include a robotic surgery device 115 configured to manipulate the medical instrument 135 based on the modified intraoperative imaging data stream.

It should be understood that that the examples and embodiments above are exemplary only, and that various embodiments may include aspects from different embodiments or may omit certain elements or operations. Any suitable combination, arrangement, or modification of the techniques discussed herein may be used.

In some aspects of the disclosure, a computer-implemented method for object recognition during a medical procedure may include receiving, from an imaging device positioned inside of a patient, an imaging scene of a target. The imaging scene may include a medical instrument. The method may further include applying a metal recognition algorithm to identify metal present in the imaging scene. The method may further include applying an object recognition algorithm to the identified metal to identify the medical instrument. The method may further include generating a modified imaging scene. The modified imaging scene may include a visual characteristic applied to the recognized medical instrument. The method may further include displaying the modified imaging scene on a display device.

In some aspects of the disclosure, a computer-implemented method for intraoperative medical instrument recognition may include receiving, from an imaging device positioned inside of a patient, an intraoperative three-dimensional (3D) video that includes anatomy of a patient and at least one medical instrument. The method may further include applying a material recognition algorithm to identify one or more objects present in the intraoperative 3D video. The method may further include applying a shape recognition algorithm to the one or more identified objects to identify the at least one medical instrument. The method may further include generating a modified intraoperative 3D video. The modified intraoperative 3D video may include a color applied to the at least one identified medical instrument. The method may further include causing a display device to output the modified intraoperative 3D video in real time.

Program aspects of the technology may be thought of as "products" or "articles of manufacture" typically in the form of executable code or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server or from a server to the mobile device. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

While the disclosed methods, devices, and systems are described with exemplary reference to transmitting data, it should be appreciated that the disclosed embodiments may be applicable to any environment, such as a desktop or laptop computer, a tablet, an augmented reality headset, a virtual reality headset, a mixed reality headset, etc. Also, the disclosed embodiments may be applicable to any type of Internet protocol.

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Thus, while certain embodiments have been described, those skilled in the art will recognize that other and further modifications may be made thereto without departing from the spirit of the invention, and it is intended to claim all such changes and modifications as falling within the scope of the invention. For example, functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations are possible within the scope of the disclosure. Accordingly, the disclosure is not to be restricted except in light of the attached claims and their equivalents.

What is claimed is:

1. A computer-implemented method for intraoperative medical instrument recognition, the computer-implemented method comprising:

receiving, from an imaging device positioned inside of a patient, a stream of intraoperative three-dimensional (3D) imaging data that includes anatomy of a patient and at least one medical instrument;

applying a material recognition algorithm to identify one or more objects formed of a predetermined material present in the intraoperative 3D imaging data, wherein the material recognition algorithm includes execution of a first machine-learning model that has been trained, based on training images of medical instruments in anatomy of one or more individuals and training material labels applied to the medical instruments, to predict a likelihood that a portion or region of input imaging data includes a particular material and to segment or generate a reconstruction of a shape formed by the particular material;

applying a shape recognition algorithm to the one or more identified objects to identify the at least one medical instrument, wherein the shape recognition algorithm includes execution of a second machine-learning model that has been trained, based on training shapes and medical instrument labels applied to the training shapes, to predict a likelihood that an input shape corresponds to a particular medical instrument; and generating a modified intraoperative imaging data stream in real-time with the receiving of the stream of intraoperative 3D imaging data, wherein the modified intraoperative imaging data stream includes a visual characteristic applied to a region of the intraoperative 3D imaging data corresponding to the at least one identified medical instrument.

2. The computer-implemented method of claim 1, further comprising:

causing a display device to output the modified intraoperative imaging data stream in real-time with the receiving of the stream of intraoperative 3D imaging data.

3. The computer-implemented method of claim 1, further comprising:

transmitting the modified intraoperative imaging data stream to a robotic surgery device configured to manipulate the at least one medical instrument based on one or more of a position, orientation, or motion of the at least one medical instrument indicated by the visual characteristic applied to the intraoperative 3D imaging data.

4. The computer-implemented method of claim 1, wherein the visual characteristic is indicative of one or more of orientation position or motion of the at least one medical instrument.

5. The computer-implemented method of claim 1, wherein:

the at least one medical instrument is a plurality of medical instruments; and a unique visual characteristic is used to identify each medical instrument.

6. The computer-implemented method of claim 1, wherein the visual characteristic includes a colorization.

7. The computer-implemented method of claim 1, wherein the intraoperative 3D imaging data includes one or more of 3D ultrasound imaging data or 3D video.

8. The computer-implemented method of claim 1, wherein:

the generating of the modified intraoperative imaging data stream is based on the stream of intraoperative 3D imaging data over a period of time, such that the generating includes predicting one or more of a future position, orientation, or motion of the at least one medical instrument or a position, orientation, or motion of an occluded portion of the at least one medical instrument; and the region where the visual characteristic is applied is based on the predicting.

9. The computer-implemented method of claim 1, wherein the training shapes used to train the second machine-learning model were generated by the first machine-learning model.

10. A computer-implemented method for object recognition during a medical procedure, comprising:

receiving, from an imaging device positioned inside of a patient, an imaging scene of a target, the imaging scene including a medical instrument;

applying a metal recognition algorithm to identify metal present in the imaging scene, wherein the metal recognition algorithm includes execution of a first machine-learning model that has been trained, based on training images of medical instruments in anatomy of one or more individuals and training metal labels applied to the medical instruments, to predict a likelihood that a portion or region of an input imaging scene includes a metal and to segment or generate a reconstruction of a shape formed by the metal;

applying an object recognition algorithm to the identified metal to identify the medical instrument, wherein the object recognition algorithm includes execution of a second machine-learning model that has been trained, based on training shapes and medical instrument labels applied to the training shapes, to predict a likelihood that an input shape corresponds to a particular medical instrument; and generating a modified imaging scene that includes a visual characteristic applied to the identified medical instrument.

11. The computer-implemented method of claim 10, further comprising:

causing a display device to output the modified imaging scene in real-time with the receiving of the imaging scene from the imaging device.

12. The computer-implemented method of claim 10, further comprising:

transmitting the modified imaging scene to a robotic surgery device configured to manipulate the medical instrument based on one or more of a position, orientation, or motion of the medical instrument indicated by the visual characteristic applied to the imaging scene.

13. The computer-implemented method of claim 10, wherein the visual characteristic is indicative of one or more of orientation, position, or motion of the medical instrument.

14. The computer-implemented method of claim 10, wherein the visual characteristic includes a colorization.

15. The computer-implemented method of claim 10, wherein the imaging device includes one or more of a 3D ultrasound probe or a 3D video camera.

16. The computer-implemented method of claim 10, wherein:

the generating of the modified imaging scene is based on data from the imaging scene taken over a period of time, such that the generating includes predicting one or more of a future position, orientation, or motion of the medical instrument or a position, orientation, or motion of an occluded portion of the medical instrument; and a location in the imaging scene where the visual characteristic is applied is based on the predicting.

17. The computer-implemented method of claim 10, wherein the training shapes used to train the second machine-learning model were generated by the first machine-learning model.

18. A system for intraoperative medical instrument recognition, comprising:

at least one medical instrument;

at least one imaging device configured to capture intraoperative three-dimensional (3D) imaging data; and an imaging analysis device that includes:

at least one memory storing:

instructions for intraoperative medical instrument recognition;

a first machine-learning model that has been trained, based on training images of medical instruments in anatomy of one or more individuals and training metal labels applied to the medical instruments, to predict a likelihood that a portion or region of an input imaging scene includes a metal and to segment or generate a reconstruction of a shape formed by the metal; and a second machine-learning device that has been trained, based on training shapes and medical instrument labels applied to the training shapes, to predict a likelihood that an input shape corresponds to a particular medical instrument; and at least one processor operatively connected to the at least one memory and configured to execute the instructions to perform operations including:

receiving, from the imaging device, a stream of intraoperative 3D imaging data that includes anatomy of a patient and at least one medical instrument at least partially inserted into the anatomy;

applying the first machine-learning model to the intraoperative 3D imaging data to identify one or more regions of the intraoperative 3D imaging data that include the metal, and to segment or generate a shape of the metal;

applying the second machine-learning model to the shape to identify the at least one medical instrument; and generating a modified intraoperative imaging data stream in real-time with the receiving of the stream of intraoperative 3D imaging data, wherein the modified intraoperative imaging data stream includes a visual characteristic applied to a region of the intraoperative 3D imaging data corresponding to the at least one identified medical instrument.

* * * * *